(12) United States Patent
Govari

(10) Patent No.: US 11,364,368 B2
(45) Date of Patent: Jun. 21, 2022

(54) GUIDEWIRE WITH AN INTEGRATED FLEXIBLE TUBE

(71) Applicant: BIOSENSE WEBSTER (ISRAEL) LTD., Yokneam (IL)

(72) Inventor: Assaf Govari, Haifa (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 374 days.

(21) Appl. No.: 16/292,985

(22) Filed: Mar. 5, 2019

(65) Prior Publication Data

US 2020/0054862 A1 Feb. 20, 2020

Related U.S. Application Data

(60) Provisional application No. 62/718,722, filed on Aug. 14, 2018.

(51) Int. Cl.
*A61M 25/09* (2006.01)
*A61B 1/07* (2006.01)
(Continued)

(52) U.S. Cl.
CPC ......... *A61M 25/09041* (2013.01); *A61B 1/07* (2013.01); *A61B 17/22* (2013.01);
(Continued)

(58) Field of Classification Search
CPC ........ A61M 25/09041; A61M 25/0127; A61M 2025/09008; A61M 2025/091; A61M 2025/09108; A61M 2025/09191; A61M 2210/0618; A61M 2210/0693; A61M 2025/0915; A61M 2025/09175; A61M 25/09; A61B 1/07; A61B 17/22; A61B 2017/22038; A61B 2017/22069; A61B 2017/22079; A61B 2017/22082;
(Continued)

(56) References Cited

U.S. PATENT DOCUMENTS 4,886,490 A * 12/1989 Shiber ................. A61B 8/12
604/22
5,372,587 A 12/1994 Hammerslag et al.
(Continued)

FOREIGN PATENT DOCUMENTS

WO WO 96/05768 2/1996
WO 9816274 A1 4/1998

OTHER PUBLICATIONS

EP 19191526.3-1132—Extended European Search Report dated Jan. 20, 2020.

*Primary Examiner* — Bhisma Mehta
*Assistant Examiner* — Neeraja Gollamudi
(74) *Attorney, Agent, or Firm* — Troutman Pepper Hamilton Sanders LLP

(57) ABSTRACT

An integrated guidewire includes a wire and a flexible tube. The wire is sized and shaped to move in an anatomical material transportation system of a patient. The flexible tube is sized and shaped to move in the anatomical material transportation system, having proximal and distal ends, the proximal-end is coupled to a device external to the patient, the flexible tube is configured to transfer fluids between the distal-end and the device, and the wire and the flexible tube are intertwined with respect to one another.

10 Claims, 3 Drawing Sheets

(51) Int. Cl.
  *A61B 17/22* (2006.01)
  *A61M 25/01* (2006.01)
(52) U.S. Cl.
  CPC ........... *A61B 2017/22038* (2013.01); *A61B 2017/22069* (2013.01); *A61B 2017/22079* (2013.01); *A61B 2017/22082* (2013.01); *A61M 25/0127* (2013.01); *A61M 2025/091* (2013.01); *A61M 2025/09008* (2013.01); *A61M 2025/09108* (2013.01); *A61M 2025/09191* (2013.01); *A61M 2210/0618* (2013.01); *A61M 2210/0693* (2013.01)
(58) Field of Classification Search
  CPC ....... A61B 1/01; A61B 1/00165; A61B 1/042; A61B 5/0084; A61B 34/20; A61B 17/24; A61B 2034/2051; A61B 2034/2065
  See application file for complete search history.

(56) References Cited

U.S. PATENT DOCUMENTS

| | | |
|---|---|---|
| 5,391,199 A | 2/1995 | Haim |
| 5,441,497 A | 8/1995 | Narciso, Jr. et al. |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 8/2003 | Acker et al. |
| 6,690,963 B2 | 2/2004 | Haim |
| 8,467,854 B2* | 6/2013 | Lewis .................. A61B 8/445 600/427 |
| 2002/0058904 A1* | 5/2002 | Boock ................ A61B 17/221 604/35 |
| 2002/0065455 A1 | 5/2002 | Haim et al. |
| 2002/0133111 A1* | 9/2002 | Shadduck .......... A61B 18/1815 604/19 |
| 2003/0120150 A1 | 6/2003 | Govari |
| 2003/0181894 A1 | 9/2003 | Neuberger |
| 2004/0068178 A1 | 4/2004 | Govari |
| 2004/0215109 A1* | 10/2004 | Pingleton ............. A61M 25/09 600/585 |
| 2005/0177220 A1* | 8/2005 | Laizzo .................. A61B 5/283 607/126 |
| 2006/0074442 A1 | 4/2006 | Noriega et al. |
| 2006/0106443 A1* | 5/2006 | Michael ................ A61N 1/056 607/122 |
| 2009/0112128 A1 | 4/2009 | Schiff et al. |
| 2009/0292225 A1* | 11/2009 | Chen ............... A61M 25/09033 600/585 |
| 2014/0236120 A1* | 8/2014 | Tsai .................. A61M 25/0136 604/506 |
| 2018/0207396 A1* | 7/2018 | Franklin ........... A61M 25/0043 |

* cited by examiner

FIG. 3
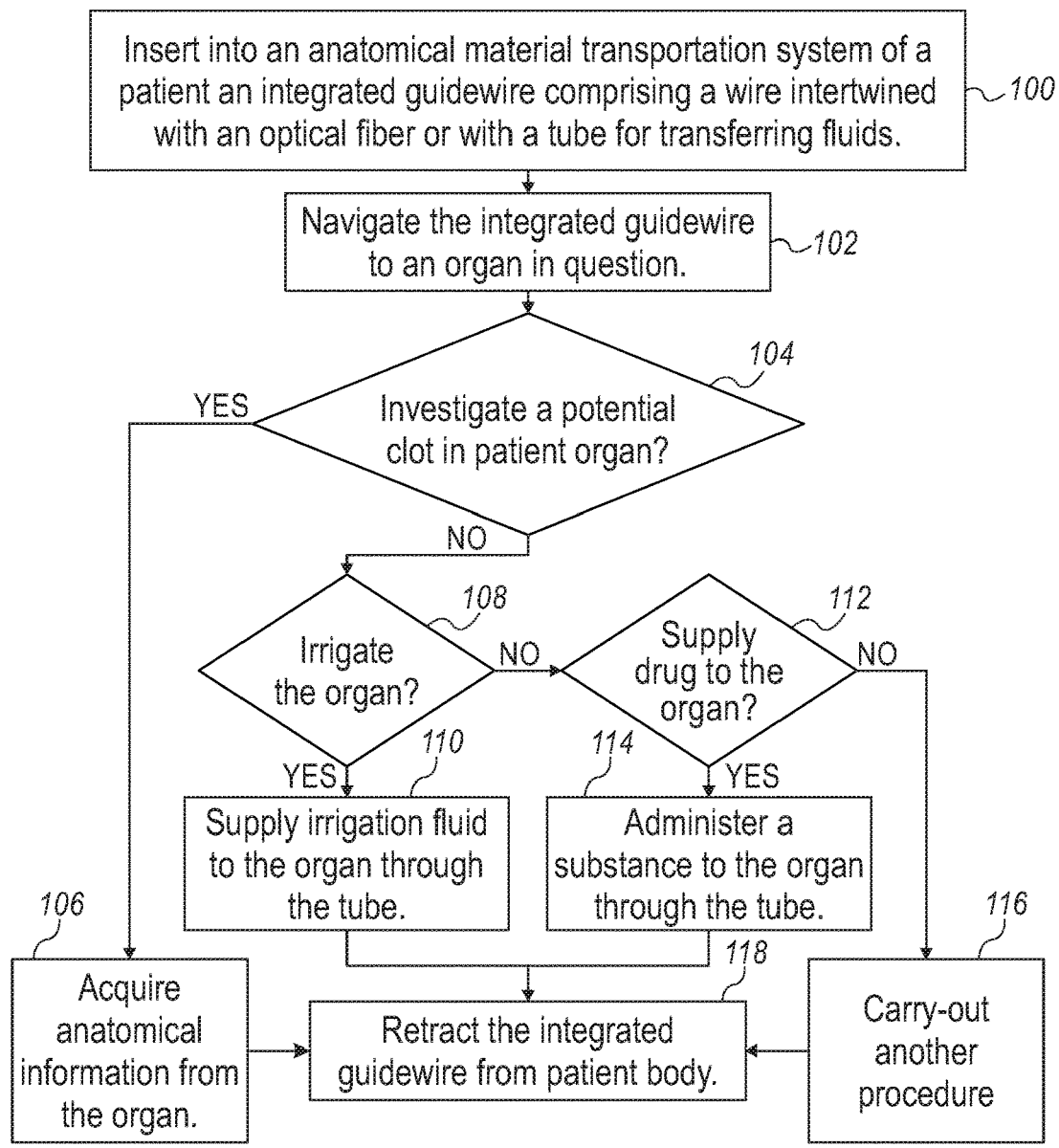
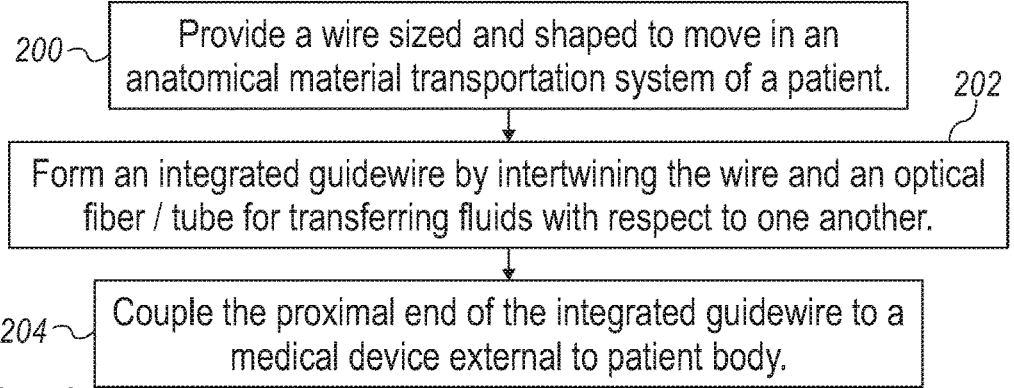
FIG. 4

GUIDEWIRE WITH AN INTEGRATED FLEXIBLE TUBE

CROSS-REFERENCE TO RELATED APPLICATIONS

This application claims the benefit of U.S. Provisional Patent Application 62/718,722, filed Aug. 14, 2018, whose disclosure is incorporated herein by reference.

FIELD OF THE INVENTION

The present invention relates generally to medical devices, and particularly to methods and systems for producing integrated guidewires and for applying these guidewires in medical procedures.

BACKGROUND OF THE INVENTION

Guidewires are used in various medical applications, such as in neurology, cardiology and sinuplasty.

For example, U.S. Patent Application Publication 2003/0181894 describes a device and method for preventing restenosis and streamlining an angioplasty procedure. The device and method provide a fiber-optic guidewire, or, alternatively, a light-conducting catheter, to decrease the size of the angioplasty device, decrease the overall time of the procedure, and increase the safety of the procedure.

U.S. Pat. 5,441,497 describes a light diffusing guidewire which has the ability to deliver light to luminal surfaces such as blood vessels for the diagnosis and treatment of medical conditions. The guidewire has an elongate body portion having a proximal end and a distal (invasive) end. A portion of the body portion transmits light from the proximal end to a light diffusing element within the body portion near the distal end.

U.S. Patent Application Publication 2006/0074442 describes a deflectable and torqueable hollow guidewire device for removing occlusive material and passing through occlusions and other materials in a body lumen. The hollow guidewire generally comprises an elongate, tubular guidewire body that has an axial lumen. A mechanically moving core element is positioned at or near a distal end of the tubular guidewire body and extends through the axial lumen.

U.S. Pat. No. 5,372,587 describes a steerable tubular sheath comprising an elongate flexible tubular body, having a laterally deflectable distal tip. Lateral deflection of the tip is accomplished by axial displacement of at least one pull wire extending through the housing. The housing comprises at least one central lumen extending axially therethrough, for receiving medical implements, optical fibers, suction or transmission of fluids such as for irrigation or drug delivery.

SUMMARY OF THE INVENTION

An embodiment of the present invention that is described herein provides an integrated guidewire including a wire and an optical fiber. The wire is sized and shaped to move in an anatomical material transportation system of a patient. The flexible tube has proximal and distal ends, the proximal-end is coupled to a device external to the patient, the flexible tube is configured to transfer fluids between the distal-end and the device, and the wire and the flexible tube are intertwined with respect to one another.

In some embodiments, the wire and the flexible tube are fixed directly to one another at one or more coupling points located between or at the distal-end and the proximal-end. In other embodiments, the integrated guidewire includes a fluid reservoir configured to supply the fluids to at least one of the device and the flexible tube. In yet other embodiments, the flexible tube is configured to transfer the fluids for at least one of: (i) irrigating the organ, (ii) treating an infection or a tumor in the organ, and (iii) drawing fluids out of a body of the patient.

In an embodiment, the intertwined wire and the flexible tube have, between the distal-end and the proximal-end, multiple windings around an axis of the integrated guidewire. In another embodiment, a number of the windings sets stiffness and flexibility levels of the integrated guidewire. In yet another embodiment, the windings are distributed evenly between the distal-end and the proximal-end.

In some embodiments, the windings are distributed unevenly between the distal-end and the proximal-end. In other embodiments, the integrated guidewire includes at least one of an additional flexible tube and an optical fiber configured to transfer optical signals between the distal-end and the proximal-end, and the at least one of the additional flexible tube and the optical fiber is intertwined with the wire and the flexible tube. In yet other embodiments, the anatomical material transportation system includes an anatomical system of the patient selected from a list consisting of a vasculature system, an ear-nose-throat (ENT) system, and a neurological system.

There is additionally provided, in accordance with an embodiment of the present invention, a method including inserting into an anatomical material transportation system of a patient an integrated guidewire that includes (i) a wire, which is sized and shaped to move in the anatomical material transportation system, and (ii) a flexible tube, sized and shaped to move in the anatomical material transportation system and having proximal and distal ends, the proximal-end is coupled to a device external to the patient, the flexible tube is configured to transfer fluids between the distal-end and the device, and the wire and the flexible tube are intertwined with respect to one another. The fluids are transferred between the distal-end and the device.

There is further provided, in accordance with an embodiment of the present invention, a method for producing an integrated guidewire, the method includes providing a wire which is sized and shaped to move in an anatomical material transportation system of a patient. The wire and a flexible tube are intertwined with respect to one another.

The present invention will be more fully understood from the following detailed description of the embodiments thereof, taken together with the drawings in which:

BRIEF DESCRIPTION OF THE DRAWINGS

FIG. 3 is a flow chart that schematically illustrates a method for applying an integrated guidewire in medical procedures, in accordance with an embodiment of the present invention; and FIG. 4 is a flow chart that schematically illustrates a method for producing an integrated guidewire, in accordance with an embodiment of the present invention.

DETAILED DESCRIPTION OF EMBODIMENTS

Overview

Figure 1:
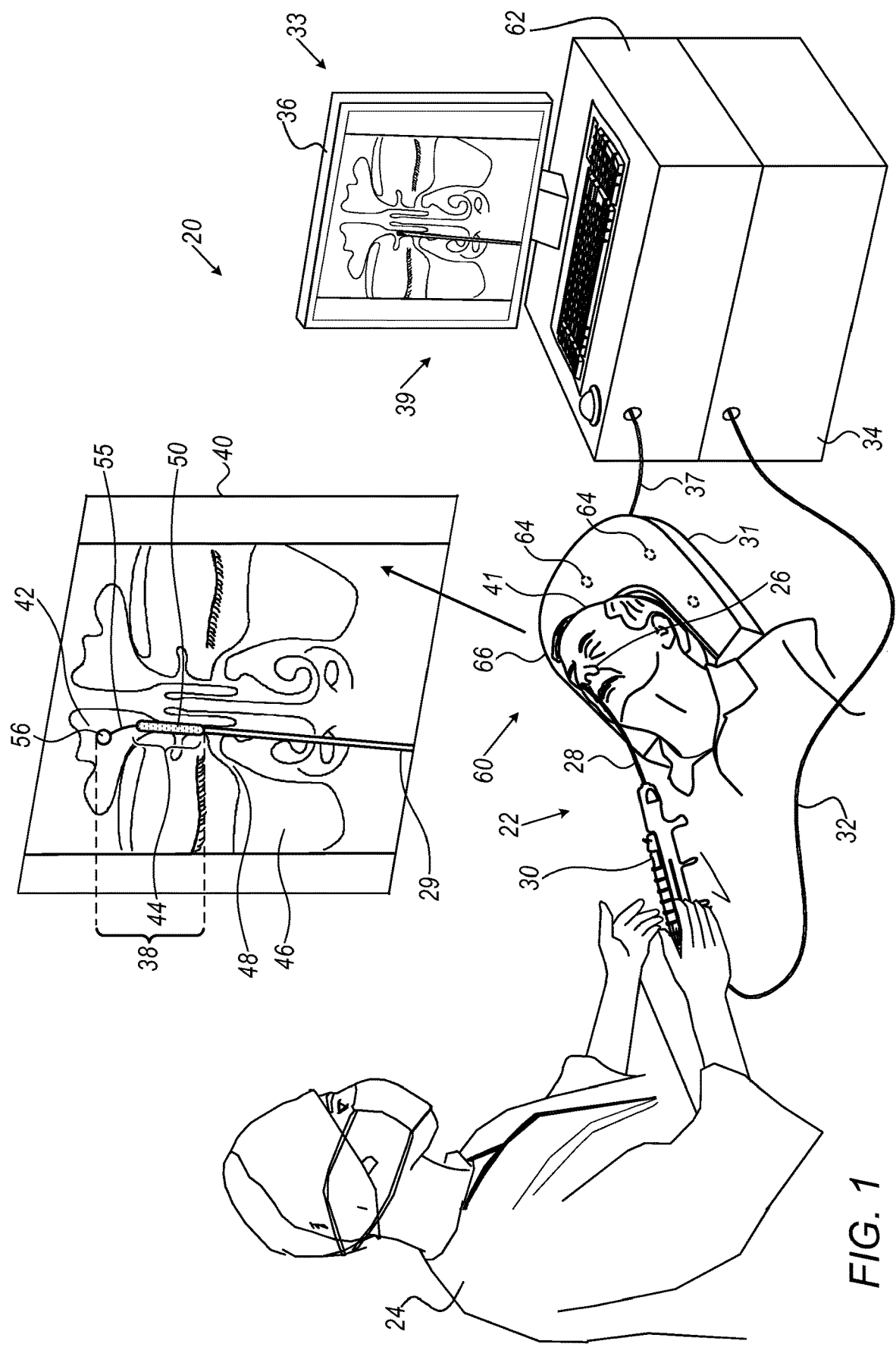
FIG. 1 is a schematic, pictorial illustration of a sinuplasty surgical system, in accordance with an embodiment of the present invention.

Embodiments of the present invention that are described hereinbelow provide improved methods and systems for producing and applying integrated guidewires comprising one or more transferring devices, such as optical fibers and/or fluid transferring tubes.

In principle, an optical fiber may be integrated in a guidewire using various methods, such as by laser cutting a spiral in a tube (to make the tube flexible) and feeding a fiber optic through the tube. In another possible method, a laser can be applied for cutting a spiral groove in a wire, wherein the optical fiber in the groove. These methods, however, are costly and difficult to apply in high volume manufacturing (HVM). Moreover, some medical procedures require drawing fluids out of a narrow lumen of a patient body (e.g., a blood vessel in the brain), or administering fluids thereto. Such procedures may be carried out using a guidewire, but guidewires with integrated tubes are difficult to manufacture.

Embodiments of the present invention provide improved techniques for producing such integrated guidewires by intertwining a wire and at least one of, (i) an optical fiber and (ii) a flexible tube, with respect to one another.

In some embodiments, an integrated guidewire comprises a wire, which is sized and shaped to move in an anatomical material transportation system of a patient, such as in the vasculature system of the brain, or in an ear-nose-throat (ENT) system of the patient. In some embodiments, the integrated guidewire further comprises one or more transferring devices such as an optical fiber and a flexible tube.

The proximal end of a transferring device is typically coupled to a device that remains external to the patient body, whereas the distal end of the transferring device is inserted into the patient body. In some embodiments, the optical fiber is configured to transfer optical signals between the distal-end and the external device, and the flexible tube is configured to transfer fluids and foreign material between the distal-end and the external device. In an embodiment, the wire and one or more transferring devices are intertwined with respect to one another.

In some embodiments, the flexible tube may be coupled to a reservoir of fluid external to the patient body, and configured to transfer the fluid from the reservoir to an organ in question. In other embodiments, the flexible tube may be coupled to a pump, which is configured to draw fluids and foreign material out of the patient body.

In an example embodiment, a physician may insert into the patient brain, an integrated guidewire comprising a wire, an optical fiber and a flexible tube, all are intertwined with respect to one another. The physician may navigate the integrated guidewire through the brain vasculature to a location that is suspected to be clotted. In this embodiment, the physician may investigate the clot by bringing the integrated guidewire in close proximity thereto, and illuminating the clot using the optical fiber. Based on the information collected in the investigation, the physician may apply the flexible tube for: (i) drawing the clot out of the patient brain, or (ii) dissolving the clot by administering a substance from the reservoir, or using any other suitable technique, such as irrigation and/or a combination of irrigation and suction of the clot out of the patient brain.

In another embodiment, the physician may sequentially apply two integrated guidewires of different types, e.g., a diagnostics guidewire comprising the intertwined wire and optical fiber, and a treatment guidewire comprising the intertwined wire and flexible tube. In this embodiment, the physician may first apply the diagnostics guidewire so as to investigate the clot, and subsequently retract the diagnostics guidewire and insert the treatment guidewire for treating the clot as described above.

The disclosed techniques improve the functionality of integrated guidewires to carry out diagnostic and treatment procedures, by enabling the integration of the wire with at least an optical fiber and/or a flexible tube. Furthermore, these techniques reduce the complexity and therefore cost of producing such integrated guidewires.

System Description

FIG. 1 is a schematic pictorial illustration of a sinuplasty procedure using a surgical system 20, in accordance with an embodiment of the present invention. In the example of FIG. 1, system 20 comprises a catheter 28, which a physician 24 inserts into a nose 26 of a patient 22 so as to treat an ear-nose-throat (ENT) disease, such as infection in one or more sinuses of patient 22. In other embodiments, system 20 may be used in other medical procedures, such as in diagnosing and treating a clot in the patient brain or other organ. Additionally or alternatively, system 20 may be used for administrating substances into, or suctioning material out of an organ or an anatomical material transportation system of patient 22, or for irrigating the organ or the anatomical material transportation system of patient 22.

Reference is now made to an inset 40 that shows a frontal anatomical view of the ENT system of patient 22. The ENT system of patient 22 comprises a frontal sinus 42 and a maxillary sinus 46. Ostia 44 and 48 connect between cavities of the nose (not shown) and sinuses 42 and 46, respectively. Catheter 28 comprises an integrated guidewire 29 having a distal end 38. In the context of the present invention the term "integrated guidewire" is also referred to below simply as "guidewire" for brevity. In an embodiment, the tip of distal end 38 may comprise a position sensor 56 attached at the end of a residual end section 55 of guidewire 29.

Catheter 28 further comprises an inflatable balloon 50, which may be configured in two positions, e.g., an expanded (inflated) position and a collapsed position. When Balloon 50 is in the collapsed position, the catheter can be navigated to the target location. The balloon is then inflated to the expanded position using a suitable fluid (e.g., a saline solution so as to anchor catheter 28 at the target location (e.g., ostium 44) in the ENT system of patient 22.

Catheter 28 further comprises a handle 30, which is located at the proximal end of catheter 28. Handle 30 is configured to control the navigation of guidewire 29 and the motion of balloon 50 along guidewire 29.

In some embodiments, system 20 further comprises a location pad 60 placed at a known position external to patient 22 lying on table 31, pad 60 comprises field-generators 64 fixed on a frame 66. In the exemplary configuration shown in FIG. 1, pad 60 comprises five field-generators 64, but may alternatively comprise any other suitable number of field-generators 64. Pad 60 further comprises a pillow (not shown) placed under a head 41 of patient 22, such that field-generators 64 are located at fixed, known positions external to head 41.

In some embodiments, system 20 comprises a console 33, which comprises a driver circuit 62 configured to drive, via a cable 37, field-generators 64 with suitable signals so as to generate magnetic fields in a predefined working volume in space around head 41. In some embodiments, console 33 comprises a processor 34, typically a general-purpose computer, with suitable front end and interface circuits for receiving, via a cable 32, signals from catheter 28. Console 33 further comprises input devices 39 and a display 36, which is configured to display data (e.g., images) received from processor 34 or inputs inserted by a user (e.g., physician 24). In an embodiment, the position of position sensor 56 is typically measured by magnetic position sensing of a catheter position tracking system comprised in system 20.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In some embodiments, system 20 may comprise an optical module, comprising a light source (not shown) that may be disposed in a suitable device of systems 20, such as in console 33 or in handle 30, and an image sensor (not shown) that may be mounted on distal end 38. In some embodiments, the light source and image sensor are optically coupled to one another via a light transferring device, such as an optical fiber, shown in FIGS. 2A, 2B and 2C below.

In other embodiments, system 20 may comprise a fluid distribution module, which comprises a fluid reservoir (not shown) filled with a fluid for medical use, such as irrigation fluid for irrigating an organ, or some substance for treating an infection or a tumor in an organ of patient 22. The reservoir may be disposed in any suitable device of systems 20, such as in console 33 or in handle 30, or in a separate tank of fluids.

In an embodiment, the fluids may be transferred from the reservoir to distal end 38 via a fluid transferring device, such as a flexible tube, shown in FIGS. 2A, 2B and 2C below, and disposed to a target organ through fluid distribution holes (not shown) formed in distal end 38. In some embodiments, the fluid transferring device may comprise a flexible irrigation tube having one or more openings, e.g., irrigation holes (not shown). The flexible irrigation tube is configured to transfer, via the irrigation holes, irrigation fluid from the reservoir to an organ in question. In other embodiments, the fluid transferring device is configured to transfer a liquid substance, such as a drug, for treating infection or a tumor in the organ in question.

In alternative embodiments, system 20 may comprise a material evacuation module (not shown) comprising a suction pump (not shown), which is configured to pump materials out of an organ of patient 22, via the fluid transferring device, e.g., into a sink (not shown) located external to patient 22.

During the sinuplasty procedure, physician 24 navigates the tip of guidewire 29 into sinus 42. In some cases, e.g., when treating infection in the sinus, it is important for the physician to anchor the distal tip of the catheter, for example by inflating balloon 50 in ostium 44. In an embodiment, balloon 50 may be 16 mm long and may have a diameter of 5 mm, such as sinuplasty balloon produced by Acclarent Inc. (catalog number RSP0516MFS), yet any other suitable balloon with other dimensions may be used in the disclosed techniques.

After inserting distal end 38 into the ENT system, physician 36 navigates balloon 50 to ostium 44. Note that, typically, balloon 50 does not comprise a position sensor and is not otherwise imaged on display 36. To perform the treatment safely and efficiently, it is important to position balloon 50 accurately within ostium 44. For example, positioning balloon 50 in the nose cavity, short of ostium 44, may not allow the physician to anchor end section 55 within sinus 42, whereas positioning the balloon within sinus 42, deeper than ostium 44, may disturb the physician in treating the infection therein.

In the example of FIG. 1, balloon 50 is used for anchoring end section 55 within sinus 42. In alternative embodiments, any other suitable device may be positioned using the disclosed techniques, instead of balloon 50. Such a device may comprise, for example, an alternative anchoring device for anchoring the end section or for any other diagnostic or treatment purpose. For example, a balloon may be used for treating cardiac arrhythmia at a pulmonary vein (PV) in a PV isolation procedure. In other applications, a drug dispensing device or a stent may be navigated to a specific location in a human organ, using the techniques described above.

In some embodiments, processor 34 is configured to assist physician 24 to position balloon 50 accurately within ostium 44. FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description.

Processor 34 may be programmed in software to carry out the functions that are used by the system, and to store data in a memory (not shown) to be processed or otherwise used by the software. The software may be downloaded to the processor in electronic form, over a network, for example, or it may, alternatively or additionally, be provided on non-transitory tangible media, such as optical, magnetic or electronic memory media. Alternatively, some or all of the functions of processor 34 may be carried out by dedicated or programmable digital hardware components.

In some embodiments, catheter 28 and guidewire 29 may be used in applying medical procedures to various human anatomical systems, such as but not limited to the vasculature system, ENT system, neurological system and patient heart. In an example embodiment, guidewire 29 may comprise an optical fiber (shown in FIG. 2 below) that may be used for illuminating the inner lumen of the blood vessels in the brain of patient 22 so as to investigate a clot in the brain or a tear in a blood vessel, or for any other diagnostics or treatment purpose in any organ or material transportation system of patient 22, as will be described in detail below. In another exemplary embodiment, guidewire 29 may comprise a flexible tube (shown in FIG. 2 below) that may be used for irrigating an organ of patient 22 (e.g., for cooling the organ during ablation), or for administering a substance into an organ of patient 22 (e.g., for treating infection or a tumor), or for suctioning some material to be removed out of an organ of the patient.

Integrated Guidewire Comprising an Optical Fiber and/or a Flexible Tube

Figure 2C:
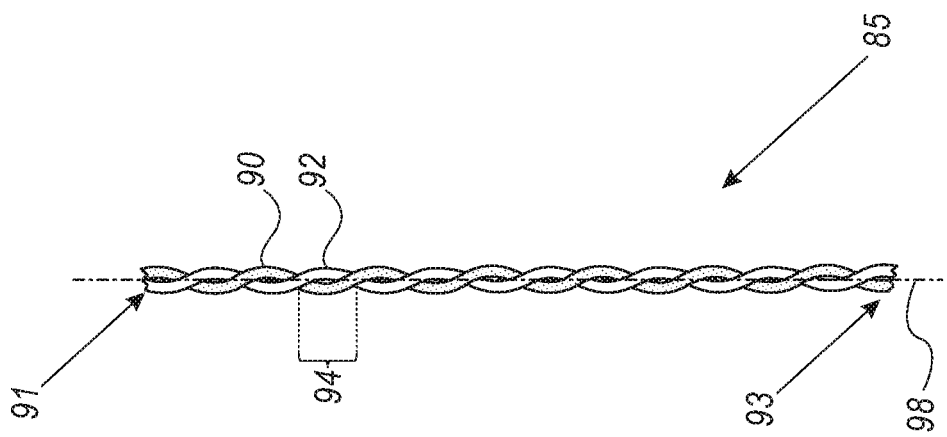
FIGS. 2A-2C are schematic, pictorial illustrations of an integrated guidewire, in accordance with an embodiment of the present invention.
Figure 2B:
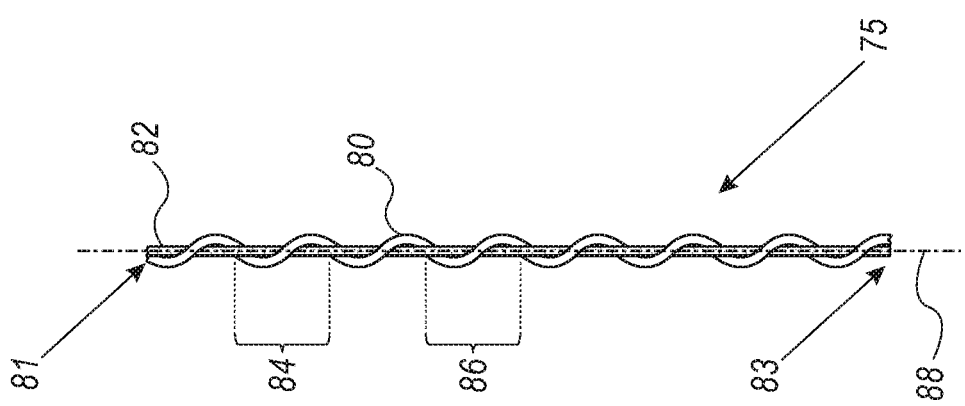
Figure 2A:
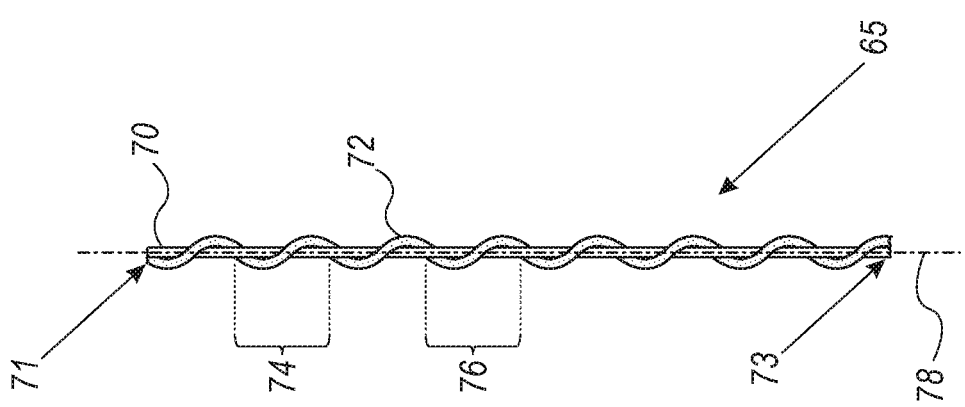

FIG. 2A is a schematic, pictorial illustration of an integrated guidewire 65, in accordance with an embodiment of the present invention. Guidewire 65 may replace, for example, guidewire 29 of FIG. 1 above. In some embodiments, guidewire 65 comprises a wire 70, which is sized and shaped to move in an anatomical material transportation system of patient 22. The transportation system may comprise ostia 44 and 48 and sinuses 42 and 46 of the ENT system shown in the example of FIG. 1, or blood vessels connecting between the heart (not shown) and any organ of patient 22, such as the brain.

In some embodiments, wire 70 is made from any suitable biocompatible material, such as an alloy of nickel-titanium, stainless steel, titanium, nickel, or from gold, or platinum. In other embodiments, wire 70 is made from two or more parts, one of which comprises a core, made from any suitable material, coated with a biocompatible material.

In some embodiments, guidewire 65 comprises a transferring device 72 having a proximal end 73 and a distal end 71, such that wire 70 and transferring device 72 are intertwined with respect to one another. In the configuration of FIG. 2A, wire 70 is laid out straight and aligned with a longitudinal axis 78 of guidewire 65, whereas transferring device 72 is wound around axis 78 and is coupled to an outer surface of wire 70. In some embodiments, transferring device 72 may comprise an optical fiber which is coupled to a light source (not shown), and is configured to transfer optical signals between the light source and distal end 71.

In an example embodiment, physician 24 may apply handle 30 for moving guidewire 65 in a blood vessel of the patient brain so as to bring distal end 71 adjacent to a clot in the brain. In this embodiment, the optical fiber transfers light from the light source toward the distal end so as to illuminate a section of the brain and the clot, and further transfers light that is reflected by the brain and clot back to the image sensor at the proximal end as described in FIG. 1 above, so as to acquire anatomical information on the clot and the brain section.

In another embodiment, transferring device 72 may comprise a flexible tube, which is coupled to the fluid reservoir described in FIG. 1 above, and is configured to transfer fluids between the reservoir and distal end 71. In an embodiment, transferring the fluid may be used for irrigating an organ, for example, during an ablation procedure. Alternatively, the flexible tube may be used for administering medication from the reservoir to an organ of patient 22, for treating the infection or tumor as described above.

In alternative embodiments, transferring device 72 may comprise the flexible tube described above, which is coupled to a pump and configured to draw material, such as infection or any undesired material, from the body of patient 22. In these embodiments, distal end 71 of the flexible tube is disposed in the organ in question, and proximal end 73 is coupled to the pump and sink described in FIG. 1 above.

In some embodiments, during the production of integrated guidewire 65, transferring device 72 is wound around wire 70, thereby forming multiple windings, such as windings 74 and 76 having a predefined pitch size. It will be understood that the pitch size and the number of windings may be varied so as to obtain a desired tradeoff between flexibility and stiffness of integrated guidewire 65. In the example embodiment of FIG. 2A, integrated guidewire 65 comprises eight windings of transferring device 72 around wire 70. In another embodiment, the guidewire may comprise only five windings, resulting in lower stiffness and higher flexibility compared to the example embodiment of FIG. 2A. In other words, a smaller pitch size results in higher stiffness and lower flexibility of the integrated guidewire.

Note that the pitch size may be uniform, or may vary, along the integrated guidewire, so as to obtain different levels of stiffness and flexibility along the integrated guidewire.

In some embodiments, transferring device 72 and wire 70 are cemented to one another at selected locations along integrated guidewire 65, typically including distal end 71 and proximal end 73. For example, transferring device 72 and wire 70 may be coupled to one another at least at one coupling point located between distal-end 71 and proximal-end 73. In the context of the present invention, the term "cemented" refers to coupling between transferring device 72 and wire 70 using any suitable coupling technique, such as gluing or soldering. In some embodiments, the materials used for cementing between device 72 and wire 70 are typically biocompatible, or coated with a biomaterial after the cementing process.

The various configurations of integrated guidewire 65 are depicted purely by way of example. In alternative embodiments, guidewire 65 may comprise any suitable number and types of transferring devices wound around wire 70 in any suitable winding configuration. For example, integrated guidewire 65 may comprise two or more transferring devices intertwined around axis 78, on the outer surface of wire 70.

FIG. 2B is a schematic, pictorial illustration of an integrated guidewire 75, in accordance with another embodiment of the present invention. Guidewire 75 may replace, for example, guidewire 29 of FIG. 1 above. In some embodiments, integrated guidewire 75 comprises a wire 80 having similar properties to wire 70 of FIG. 2A, and a transferring device 82 having a proximal end 83 and a distal end 81, such that wire 80 and transferring device 82 are intertwined with respect to one another.

In the configuration of FIG. 2B, transferring device 82 is laid out straight and aligned with a longitudinal axis 88 of guidewire 75, whereas wire 80 is wound around axis 88 and is coupled to an outer surface of transferring device 82.

In some embodiments, transferring device 82 may comprise an optical fiber which is coupled to the light source (not shown), described in FIG. 1 above, and is configured to transfer optical signals between the light source and distal end 81, as also described in FIG. 2A above.

In another embodiment, transferring device 82 may comprise a flexible tube, which is coupled to the fluid reservoir described in FIG. 1 above. In the form of the flexible tube, transferring device 82 is configured to transfer fluids, such as irrigation fluids or medication substance, between the reservoir and distal end 81, as described in FIG. 2A above.

In alternative embodiments, transferring device 82 may comprise a flexible tube, which is coupled to a pump and configured to draw material, such as infection or any undesired material, from the body of patient 22. In these embodiments, distal end 81 of the flexible tube is disposed in the organ in question, and proximal end 83 is coupled to the pump and sink described in FIG. 1 above.

In some embodiments, during the production of integrated guidewire 75, wire 80 is wound around transferring device 82, thereby forming multiple windings, such as windings 84 and 86 having an even or a variable pitch size. In these embodiments, the windings are distributed evenly along integrated guidewire 75, between distal end 81 and proximal end 83. As described in FIG. 2A above, the pitch size and the number of windings may vary along axis 88 so as to determine the flexibility and stiffness of each section of integrated guidewire 75.

In some embodiments, transferring device 82 and wire 80 are cemented to one another, using the techniques described in FIG. 2A above.

FIG. 2C is a schematic, pictorial illustration of an integrated guidewire 85, in accordance with another embodiment of the present invention. Guidewire 85 may replace, for example, guidewire 29 of FIG. 1 above. In some embodiments, integrated guidewire 85 comprises a wire 90 having similar properties to wire 70 of FIG. 2A, and a transferring device 92 having a proximal end 93 and a distal end 91.

During the production of integrated guidewire 85, transferring device 92 and wire 90 are intertwined with respect to one another as in a twisted pair configuration, and subsequently, are cemented to one another, using the cementing techniques described in FIG. 2A above.

In some embodiments, during the production of guidewire 85, transferring device 92 and wire 90 are coupled to one another, permanently or temporarily, at one end (e.g., at proximal end 93). Subsequently, device 92 and wire 90 are braided relative to one another around a longitudinal axis 98 of guidewire 85, such that neither wire 90 nor transferring device 92 are laid out straight.

After shaping guidewire 85 as a braid, device 92 and wire 90 may be permanently coupled to one another, typically at the distal and proximal ends, using the techniques described in FIG. 2A above.

In the example of FIG. 2C, integrated guidewire 85 has a uniform pitch 94 substantially smaller than pitch 84 of guidewire 75, resulting in thirteen windings per 5 mm of linear length in guidewire 85 compared to eight windings per 5 mm in guidewire 75. As a result, guidewire 85 has higher stiffness and lower flexibility compared to guidewire 75, assuming wires 80 and 90 are substantially identical, and using substantially identical transferring devices 82 and 92. Note that in other configurations the size of pitch 94 may vary along axis 98 of guidewire 85, so as to obtain the desired stiffness and flexibility as each section of integrated guidewire 85. In case increased stiffness is desired, the twisted pair of wire 90 and transferring device 92 may be fixed directly together using any suitable fixation technique, e.g., epoxy, polyurethane, staples or crimping bands.

In some embodiments, transferring device 92 may comprise an optical fiber which is coupled to the light source (not shown), described in FIG. 1 above, and is configured to transfer optical signals between the light source and distal end 91, as also described in FIG. 2A above.

In another embodiment, transferring device 92 may comprise a flexible tube, which is coupled to the fluid reservoir described in FIG. 1 above. In the form of the flexible tube, transferring device 92 is configured to transfer fluids, such as irrigation fluids or medication substance, between the reservoir and distal end 91, as described in FIG. 2A above.

In alternative embodiments, transferring device 92 may comprise a flexible tube, which is coupled to a pump and configured to draw material, such as infection or any undesired material, from the body of patient 22. In these embodiments, distal end 91 of the flexible tube is disposed in the organ in question, and proximal end 93 is coupled to the pump and sink described in FIG. 1 above.

The particular configurations of integrated guidewires 65, 75 and 85 are shown by way of example, in order to illustrate certain problems that are addressed by embodiments of the present invention and to demonstrate the application of these embodiments in enhancing the performance of a medical system such as system 20.

Embodiments of the present invention, however, are by no means limited to this specific sort of example integrated guidewires, and the principles described herein may similarly be applied to other sorts of integrated guidewires. In an alternative embodiment, another type of integrated guidewire may comprise two or more transferring devices. In an example embodiment, the guidewire may comprise a single wire and two flexible tube, a first tube for pumping fluids to the organ in question and a second tube for drawing material out of the patient body. The wire and the flexible tubes may be wound around the longitudinal axis of the integrated guidewire, using any suitable winding technique, such as the techniques described in FIGS. 2A-2C above. This configuration may be used to remove undesired material from patient body using a flux of incoming fluid from the first tube and using the second tube for drawing a mixture of the undesired material and the incoming fluid. In alternative embodiments, the integrated guidewire may comprise an optical fiber and a suction tube, for example, so as to investigate the clot in the brain, and if medically applicable, to draw the clot out of the brain thereafter, using the suction tube.

In other embodiments, the integrated guidewire may comprise any combination of one or more wires, wound around an axis with one or more optical fibers, and/or one or more flexible tubes, and/or any other one or more suitable types of transferring devices.

FIG. 3 is a flow chart that schematically illustrates a method for applying integrated guidewire 75 in various medical procedures, in accordance with an embodiment of the present invention. Note that integrated guidewire 75 was selected purely by way of example. In alternative embodiments, any other suitable type of integrated guidewire, such as guidewires 65 and 85 depicted above, may be applied in addition to, or instead of guidewire 75.

The method begins at a guidewire insertion step 100, with physician 24 inserting integrated guidewire 75 into an anatomical material transportation system of patient 22. As described in FIG. 2B above, guidewire 75 comprises wire 80 intertwined with transferring device 82, such as the optical fiber or the flexible tube.

At a navigation step 102, physician 24 navigates integrated guidewire 75 to an organ in question, such as the brain or frontal sinus 42 of patient 22. At a first decision step 104, physician 24 checks whether investigation of a potential clot in the brain of patient 22 is required.

When at step 104 physician 24 decides to investigate the potential clot and assuming guidewire 75 comprises the optical fiber, physician 24 may apply guidewire 75 to acquire anatomical information, such as images of the clot, at an anatomical image acquisition step 106. After concluding the acquisition of clot images, physician 24 may retract guidewire 75 out of the body of patient 22, at a guidewire retraction step 118.

At a second decision step 108, physician 24 checks whether irrigation of an organ of patient 22 is required, for example, to open a block at ostium 44 of the ENT system. When at step 108 the physician decides that irrigation is required, physician 24 may apply guidewire 75 to irrigate ostium 44, at an irrigation step 110.

After irrigating ostium 44, physician 24 may retract guidewire 75 out of the body of patient 22, at guidewire retraction step 118.

At a third decision step 112, in an embodiment, physician may identify an infection in frontal sinus 42 and has to decide whether to administer a suitable substance, such as an antibiotic drug, for treating the infection. In another embodiment, based on the images acquired at step 106, physician 24 may consider to dissolve the clot in the brain of patient 22. At a substance administration step 114, physician may apply guidewire 75 to administrate the substance into the organ in question of patient 22. For example, by administering the antibiotic drug into frontal sinus 42, or by administering a material adapted to dissolve the clot in the brain of patient 22.

After concluding substance administration step 114, physician 24 may retract guidewire 75 out of the body of patient 22, at guidewire retraction step 118.

At an alternative procedure step 116, physician 24 may decide to treat the infection in frontal sinus 42 and/or the clot in the brain of patient 22 using alternative techniques to substance administration. For example, physician 24 may apply guidewire 75 having the suction tube described, for example, in FIG. 2A above. In this embodiment, physician 24 may apply the suction tube of guidewire 75 to draw the infection from sinus 42 and/or to draw the clot from the brain of patient 22.

After concluding the material drawing at step 116, physician 24 may retract guidewire 75 out of the body of patient 22, at guidewire retraction step 118.

In some embodiments, the procedures described at steps 106, 110, 114 and 116 may be carried out separately, such that retraction step 118 concludes the method for each procedure. In other embodiments, two or more of steps 106, 110, 114 and 116 may be carried out sequentially or simultaneously without retracting guidewire 75 between the respective steps. For example, as described above, any integrated guidewire, such as guidewire 75, may comprise two transferring devices 82, such as an optical fiber and a suction tube. In these embodiments, physician may apply the optical fiber to investigate the clot, as described at step 106 above, subsequently apply the suction tube so as to draw the clot out of the brain of patient 22, and only then retract guidewire 75 out.

FIG. 4 is a flow chart that schematically illustrates a method for producing integrated guidewire 65, in accordance with an embodiment of the present invention. Note that integrated guidewire 65 was selected purely by way of example. In alternative embodiments, any other suitable type of integrated guidewire, such as guidewires 75 and 85 depicted above, may be produced in addition to, or instead of guidewire 65.

The method begins with providing wire 70, which is sized and shaped to move in the blood vessels or in any other anatomical material transportation system of patient 22, at a wire provision step 200. Note that wire 70 may alternatively be produced, for example, by cutting and shaping a section from a continuous wire. At an intertwining step 202, a production operator forms integrated guidewire 65 by intertwining between wire 70 and one or more transferring devices 72, which comprise one or more optical fibers and/or one or more flexible tubes as described above.

At a coupling step 202, which concludes the production method of integrated guidewire 65, a production operator couples the proximal end of the integrated guidewire to a medical device or system located externally to the body of patient 22. As described above, the medical devices or systems may comprise at least one of handle 30, console 33, a fluid reservoir, a pump, a light source, an image sensor, and any other suitable device, apparatus and/or system.

Although the embodiments described herein mainly address sinuplasty procedures, the methods and systems described herein can also be used in other applications, such as in neurology, cardiology and the vasculature system.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for treating a clot within a vessel in the brain of a patient, comprising:
    inserting into an anatomical material transportation system of a patient an integrated guidewire comprising:
        a wire, which is sized and shaped to move in the anatomical material transportation system; and
        a flexible tube, sized and shaped to move in the anatomical material transportation system, and having proximal and distal ends, wherein the proximal end is coupled to a device external to the patient, wherein the flexible tube is configured to transfer fluids between the distal end and the external device, and wherein the wire and the flexible tube are intertwined with respect to one another such that neither the wire nor the flexible tube are straight within an axis of the integrated guidewire; and
    transferring the fluids between the distal end and the external device; wherein
        inserting the integrated guidewire comprises inserting at least one of an additional flexible tube and an optical fiber for transferring optical signals between the distal end and the proximal end, and wherein the at least one of the additional flexible tube and the optical fiber are intertwined with the wire and the flexible tube, wherein the proximal end of the optical fiber is coupled to a light source and image sensor device external to the patient;
    transferring light via the optical fiber from the light source toward the distal end so as to illuminate a section of the brain and the clot;
    further transferring light that is reflected by the brain and clot back to the image sensor at the proximal end of the optical fiber; and
    determining to treat the clot by at least one of dissolving the clot in the brain of the patient and removing the clot from the vessel of the patient.

2. The method according to claim 1, wherein the wire and the flexible tube are fixed directly to one another at one or more coupling points located between or at the distal end and the proximal end of the flexible tube.

3. The method according to claim 1, wherein transferring the fluids comprises transferring the fluids for at least one of: (i) irrigating the brain, (ii) treating an infection or a tumor in the brain, and (iii) drawing fluids out of a body of the patient.

4. The method according to claim 1, wherein the intertwined wire and the flexible tube have, between the distal end and the proximal end of the flexible tube, multiple windings around the axis of the integrated guidewire.

5. The method according to claim 4, wherein a number of the windings sets stiffness and flexibility levels of the integrated guidewire.

6. The method according to claim 4, wherein the windings are distributed evenly between the distal end and the proximal end of the flexible tube.

7. The method according to claim 4, wherein the windings are distributed unevenly between the distal end and the proximal end of the flexible tube.

8. The method according to claim 1, wherein inserting the integrated guidewire comprises inserting the integrated guidewire into an anatomical system of the patient selected from a list consisting of a vasculature system, an ear-nose-throat (ENT) system, and a neurological system.

9. The method according to claim 1, wherein transferring the fluids comprises drawing fluids from the patient to the device.

10. The method according to claim 1, further comprising drawing fluids and foreign material out of a body of the patient.

\* \* \* \* \*